United States Patent [19]

Kees

[11] Patent Number: 5,274,111
[45] Date of Patent: Dec. 28, 1993

[54] TRIFLUOROMETHYL SUBSTITUTED 1H-PYRAZOLES AND DERIVATIVES THEREOF

[75] Inventor: Kenneth L. Kees, Plainsboro, N.J.

[73] Assignee: American Home Products Corporation, New York, N.Y.

[21] Appl. No.: 56,967

[22] Filed: May 3, 1993

Related U.S. Application Data

[63] Continuation-in-part of Ser. No. 864,990, Apr. 7, 1992.

[51] Int. Cl.$^5$ ............................................. C07D 231/20
[52] U.S. Cl. ........................................................ 548/366.1
[58] Field of Search ........................................ 548/366.1

[56] References Cited

U.S. PATENT DOCUMENTS 3,978,077  8/1976  Möller et al. .................... 548/366.1
4,099,011  7/1978  Möller et al. .................... 548/366.1

FOREIGN PATENT DOCUMENTS 499699  10/1991  European Pat. Off. .

*Primary Examiner*—Robert W. Ramsuer
*Attorney, Agent, or Firm*—Richard K. Jackson

[57] ABSTRACT

The compounds of the formulae:

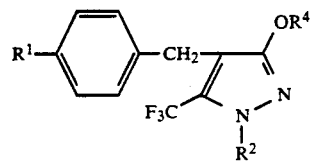

and

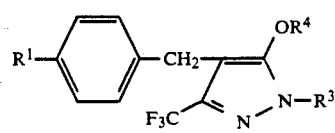

in which
$R^1$ is alkyl, perfluoroalkyl, alkoxy, perfluoroalkoxy of 1 to 6 carbon atoms, alkylthio, perfluoroalkylthio, alkylsulfinyl, alkylamino, halo, alkanoyl, 1-hydroxyalkyl or 1-(hydroxyimino) alkyl;
$R^2$ is hydrogen or alkyl of 1 to 3 carbon atoms;
$R^3$ is alkyl of 1 to 3 carbon atoms;
$R^4$ is alkyl of 1 to 6 carbon atoms;

or a pharmaceutically acceptable salt thereof, are antihyperglycemic agents.

10 Claims, No Drawings

TRIFLUOROMETHYL SUBSTITUTED 1H-PYRAZOLES AND DERIVATIVES THEREOF

RELATED APPLICATIONS

This application is a continuation-in-part of application Ser. No. 07/864,990, filed Apr. 7, 1992.

BACKGROUND OF THE INVENTION

Japanese patent 55/157504 discloses a group of herbicidal compounds of the formula:

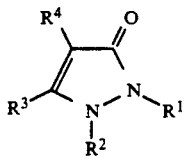

in which $R^1$ is hydrogen or alkyl; $R^2$ is alkyl, alkoxycarbonylmethyl or phenyl; $R^3$ is alkyl; and $R^4$ is hydrogen, alkanoyl, or a substituted or unsubstituted benzyl or benzoyl group.

Japanese patent 55/113706 discloses a group of herbicidal compounds of the formula:

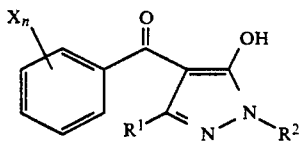

in which $R^1$ and $R^2$ are alkyl, formyl, haloalkyl, hydroxyalkyl, phenyl or halophenyl; X is alkyl, alkoxy, nitro or halo and n is 0-2.

U.S. Pat. No. 4,113,957 discloses 1-substituted-5-acyloxypyrazoles of the formula:

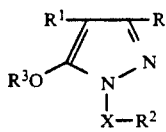

in which R is H, $-CF_3$, alkyl, aryl, heteroaryl or aralkyl; $R^1$ is H, alkyl, aryl or aralkyl; X is alkylene or alkylene-O— or alkylene-S—; $R^2$ is aryl, $CF_3$, alkyl, alkenyl, alkoxy, alkylamino, $-CN$, OCF, $-NO_2$, $-CONH_2$, $-SO_2NH_2$ or $-SO_n$ alkyl. Other variables also apply to the structural formula. These compounds are disclosed to be diuretics, saluretics, antithrombotics and antihypertensives.

EP Application 208,874 discloses a group of compounds of the formula:

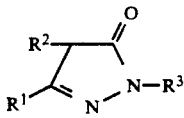

in which $R^1$ is H, aryl, alkyl, or alkoxycarbonylalkyl; $R^2$ is hydrogen, aryloxy, arylmercapto, alkyl or hydroxyalkyl; $R^1$ and $R^2$ together may be alkylene; $R^3$ is hydrogen, alkyl, cycloalkyl, hydroxyalkyl, benzyl, naphthyl or phenyl, substituted or unsubstituted.

U.S. Pat. No. 3,978,077 to Moller et al discloses on column 4, structure IX as

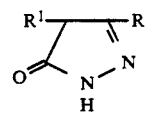

in which R, among other variables, may be trifluoromethyl and $R^1$, among many other things, may be aralkyl substituted by lower alkoxy (col. 1, lines 48-58). These compounds are disclosed as intermediates for production of various N-substituted pyrazolones. No final product containing the trifluoromethyl group or the substituted benzyl group is disclosed to have been made by that intermediate. Compounds substituted in that manner were always prepared by a process not involving alkylation of a pyrazolone intermediate.

EP 449,699, published Oct. 2, 1991, discloses an extremely broad genus of compounds which can be interpreted to embrace a nitro substituted benzyl substituent in 4-position and an alkyl group in 5-position of a pyrazole nucleus.

U.S. Pat. No. 4,099,011 to Moller et al alleges the equivalence of an alkyl group and the trifluoromethyl group on a related pyrazole ring. This patent also equates the nitro group with an alkyl or alkoxy group as substituents on a benzyl group in the related antihypertensive agents.

BRIEF DESCRIPTION OF THE INVENTION

This invention provides a group of 3-alkoxy-4-(substituted benzyl)-5-trifluoromethyl-1H-parazoles and their N-substituted derivatives. The compounds of this invention are potent, orally active antihyperglycemic agents useful in the treatment of non-insulin dependent diabetes mellitus.

DETAILED DESCRIPTION OF THE INVENTION

In accordance with this invention, there is provided a group of compounds of the formulae:

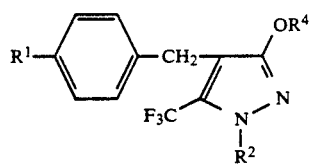

and

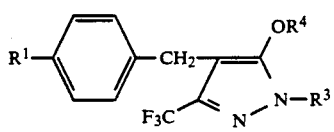

in which
$R^1$ is alkyl of 1 to 6 carbon atoms, perfluoroalkyl of 1 to 6 carbon atoms, alkoxy of 1 to 6 carbon atoms, perfluoroalkoxy of 1 to 6 carbon atoms, alkylthio of 1 to 6 carbon atoms, perfluoroalkylthio of 1 to 6 carbon atoms, alkylsulfinyl of 1 to 6 carbon atoms, alkylamino of 1 to 6 carbon atoms, halo, alkanoyl of 2 to 6 carbon atoms, 1-hydroxyalkyl of 1 to 6 carbon atoms or 1-(hydroxyimino) alkyl of 1 to 6 carbon atoms;
$R^2$ is hydrogen or alkyl of 1 to 3 carbon atoms;
$R^3$ is alkyl of 1 to 3 carbon atoms;
$R^4$ is alkyl of 1 to 6 carbon atoms;
or a pharmaceutically acceptable salt thereof.

The preferred compounds are those best depicted by the formula:

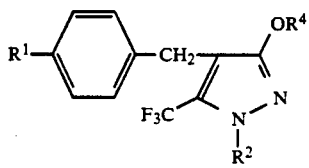

in which
$R^1$ is alkyl or alkylthio of 1 to 3 carbon atoms;
$R^2$ is alkyl of 1 to 3 carbon atoms; and
$R^4$ is alkyl of 1 to 6 carbon atoms;
or a pharmaceutically acceptable salt thereof and those best depicted by the formula:

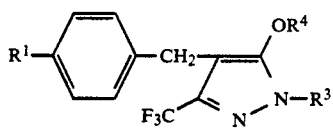

in which
$R^1$ is alkyl or alkylthio of 1 to 3 carbon atoms;
$R^3$ is alkyl of 1 to 3 carbon atoms; and
$R^4$ is alkyl of 1 to 6 carbon atoms;
or a pharmaceutically acceptable salt thereof.

In the compounds disclosed above, the alkyl group representing $R^{1-4}$ are methyl, ethyl, propyl, isopropyl, butyl, tert-butyl, pentyl, hexyl, and the like, the methyl, ethyl, propyl and isopropyl groups being preferred; the perfluoroalkyl groups are trifluoromethyl, pentafluoroethyl or heptafluoropropyl; the alkoxy groups correspond in size to the alkyl groups defined above; and the halogens are chloro, bromo, fluoro and iodo, the first two being preferred.

The pharmaceutically acceptable salts of the compounds of this invention where $R^1$ is alkylamino may be derived from known inorganic and organic acids such as hydrochloric, oxalic, tartaric, fumaric, lactic, phosphoric, p-toluene sulfonic, formic, hydrobromic, maleic, sulfamic acids, and the like. Salts of the pyrazole group with bases are readily formed. Suitable cations are the alkali metals (Na or K) the alkaline earth metals (Mg or Ca), ammonium or primary or secondary alkyl amines.

The compounds of this invention are prepared conventionally by the reaction of:

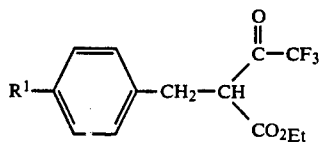

with hydrazine.

The following examples illustrate the preparation of representative compounds of this invention.

EXAMPLE 1

3-Methoxy-4-[4-(methylthiophenyl)methyl]-5-(trifluoromethyl)-1H-pyrazole

A solution of 4-methylthiobenzyl alcohol (20 g) and carbon tetrabromide (47.4 g) in dichloromethane (450 mL) was cooled to 0° C. under $N_2$ atmosphere. Triphenyl phosphine (37.4 g) was added portionwise over 0.5 hours and the resulting mixture allowed to warm gradually to ambient temperature. The reaction mixture was poured onto saturated aqueous NaCl solution. The organic phase was dried over $MgSO_4$, concentrated in vacuo on the rotary evaporator and filtered through a silica gel column with the aid of dichloromethane. Volatile materials were removed on the rotary evaporator and the residue was triturated with hot heptane. The heptane solution was allowed to stand at room temperature overnight, filtered and concentrated. This process was repeated twice with petroleum ether to give a quantitative yield of 4-(methylthiophenyl)methyl bromide as a yellow mobile oil.

Sodium hydride (2.76 g, 60% oil dispersion) in 1,2-dimethoxyethane (50 mL) was cooled to 0° C. with stirring under $N_2$ atmosphere. Ethyl 4,4,4-trifluoromethyl acetoacetate (12.7 g) was added dropwise at a rate so as to control $H_2$ evolution. When the addition was complete the homogeneous solution was warmed to reflux temperature and a solution of 4-(methylthiophenyl)methyl bromide (15 g) in 1,2-dimethoxyethane (100 mL) was added. The reaction mixture was refluxed 15 hours, cooled to room temperature, and volatile materials were removed in vacuo on the rotary evaporator. The residue was partitioned between 1N aqueous HCl solution and ethyl acetate. The organic phase was washed with additional 1N HCl solution (2×50 mL) and with saturated aqueous NaCl solution, dried over $MgSO_4$ and concentrated. The residue was kugelrohr distilled at reduced pressure (~0.5 mm Hg). Excess starting β-keto ester was collected below 100° C. oven temperature and the desired ethyl-α-(trifluoroacetyl)-3-(4-methylthiophenyl) propionate (12.2 g) was collected at 115°-140° C. oven temperature.

A mixture of ethyl α-(trifluoroacetyl)-3-(4-methylthiophenyl) propionate (6 g), anhydrous hydrazine (0.92 mL) and toluene were refluxed 15 hours. The reaction mixture was cooled to ambient temperature and concentrated to a tan solid. The residue was triturated with hot toluene (steam bath). The solution was decanted and the product crystallized on standing. The compound, 1,2-dihydro-4-[(4-methylthiophenyl)methyl]-5-(trifluoromethyl)-3H-pyrazole-3-one, obtained as white crystals, weighed 1.08 g after 15 hours in an abderhalden apparatus (ethanol, reflux), mp 147.5°–148.5° C.

Elemental analysis for: $C_{12}H_{11}F_3N_2OS$: Calc'd: C, 50; H, 3.85; N, 9.72; Found: C, 50.27; H, 3.77; N, 9.41.

A mixture of 1,2-dihydro-4-[(4-methylthiophenyl)methyl]-5-(trifluoromethyl)-3H-pyrazole-3-one (2 g), anhydrous potassium carbonate (1.44 g, pulverized) and acetonitrile (25 mL) refluxed for 1 hour, cooled to room temperature and methyl iodide added to the stirred mixture in portions (4×0.44 mL) over 2 days. The reaction was diluted with enough water to dissolve all salts and the mixture partitioned between ethyl acetate and saturated brine solution. The extracts were washed with saturated brine, dried over $MgSO_4$, concentrated and the residue chromatographed on silica gel (35 wt. eq.).

Elution with 10% ethyl acetate/hexane provided the title compound as a white solid, mp 115°–117° C.

Elemental analysis for: $C_{13}H_{13}F_3N_2OS$: Calc'd: C, 51.65; H, 4.33; N, 9.27; Found: C, 51.97; H, 4.28; N, 8.95.

EXAMPLE 2

3-Methoxy-1-methyl-4-[4-(methylthiophenyl)methyl]-5-(trifluoromethyl)pyrazole

The title compound was prepared as in Example 1 except that the reaction was carried out at reflux for 3 days with 5 portions of methyl iodide periodically added to the reaction mixture. Chromatography on silica gel, elution with hexane provided the title compound as a waxy white solid, mp 31°–34° C.

Elemental analysis for: $C_{14}H_{15}F_3N_2OS$: Calc'd: C, 53.16; H, 4.78; N, 8.86; Found: C, 53.05; H, 4.78; N, 8.89.

EXAMPLE 3

4-[4-(Ethylphenyl)methyl]-3-(methoxy)-5-(trifluoromethyl)-1H-pyrazole

The title compound was prepared as in Example 1 starting from 1,2-dihydro-4-[(4-ethylphenyl)methyl]-5-(trifluoromethyl)-3H-pyrazol-3-one (which was also prepared in the same manner as the pyrazolone of Example 1, except that anhydrous 1,2-dimethoxyethane was used as solvent in the reaction with hydrazine and recrystallization from hot hexane- diethyl ether mixture was employed to obtain the compound as a yellow powder, mp 128°–130° C., elemental analysis for: $C_{13}H_{13}F_3N_2O$: Calc'd: C, 57.78; H, 4.85; N, 10.37; Found: C,57.69; H, 4.60; N, 10.39).

Chromatography on silica gel, elution with 5% ethyl acetate/hexane provided the title compound as a yellow oil.

Elemental analysis for: $C_{14}H_{15}F_3N_2O \cdot 0.75\ H_2O$: Calc'd: C, 60.4; H, 5.74; N, 9.39; Found: C, 60.1; H, 5.74; N, 9.13.

EXAMPLE 4

4-[4-(Ethylphenyl)methyl]-3-(methoxy)-1-(methyl)-5-(trifluoromethyl)-pyrazole

The title compound was prepared as in Example 2 from 1,2-dihydro-4-[(4-ethylphenyl)methyl]-5-(trifluoromethyl)-3H-pyrazol-3-one. Chromatography on silica gel, elution with 5% ethyl acetate/hexane provided the title compound as a yellow oil.

Elemental analysis for: $C_{15}H_{17}N_2F_3O$: Calc'd: C, 60.4; H, 5.74; N, 9.39; Found: C, 60.1; H, 5.74; N, 9.13.

EXAMPLE 5

3-Ethoxy-1-(ethyl)-4-[4-(methylthiophenyl)methyl]-5-(trifluoromethyl)-pyrazole

The title compound was prepared as in Example 2 from 1,2-dihydro-4-[(4-methylthiophenyl)methyl]-5-(trifluoromethyl)-3H-pyrazole-3-one and ethyl iodide. Chromatography on silica gel, elution with 10% ethyl acetate/hexane provided the title compound as a colorless oil (least polar isomer).

Elemental analysis for: $C_{16}H_{19}F_3N_2OS$: Calc'd: C, 55.8; H, 5.56; N, 8.13; Found: C, 55.92; H, 5.37; N, 8.07.

EXAMPLE 6

5-Ethoxy-1-(ethyl)-4-[4-(methylthiophenyl)methyl]-3-(trifluoromethyl)pyrazole

The title compound was prepared in the same reaction as Example 5. The title compound was the more polar isomer eluted from silica gel, as a yellow oil.

Elemental analysis for: $C_{16}H_{19}F_3N_2OS$: Calc'd: C, 55.8; H, 5.56; N, 8.13; Found: C, 55.87; H, 5.61; N, 8.14.

Note: the structural assignments for the isomers—Examples 5 and 6 were made on the basis of $^{13}C$-NMR as indicated.

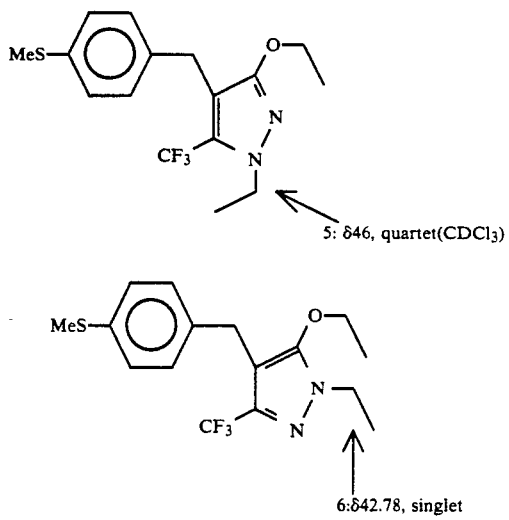

EXAMPLE 7

5-Methoxy-1-(methyl)-4-[(4-methylthiophenyl)methyl]-3-(trifluoromethyl)pyrazole

The title compound was prepared as in Example 1 from 1-methyl-4-[(4-methylthiophenyl)methyl]-3-(trifluoromethyl)-2H-pyrazol-5-one, which was also prepared as in Example 1 except that methylhydrazine was used instead of hydrazine and recrystallization from toluene-hexane mixture provided the intermediate compound as off-white crystals, mp 138°–139° C.

Elemental analysis for: $C_{13}H_{13}F_3N_2OS$: Calc'd: C, 51.65; H, 4.33; N, 9.27; Found: C, 51.93; H, 4.39; N, 8.91.

The title compound, as an amber oil, was analytically pure as isolated from aqueous work-up.

Elemental analysis for: $C_{14}H_{15}F_3N_2OS$: Calc'd: C, 53.15; H, 4.78; N, 8.85; Found: C, 53.24; H, 5.05; N, 8.76.

The antihyperglycemic activity of the compounds of this invention was established by subjecting them to the following standard experimental procedure for that purpose:

Two to seven month old, male, db/db mice (35–60 g) are placed in seven groups of four (drug group) to six (vehicle group) mice. The test compound is administered in single oral doses, once a day, for four days. The control group receives vehicle only over the same period. Ciglitazone is employed as a positive control, by gavage administration of 100 mg/kg/day. Food is supplied to the mice ad libitum during the test procedure. On the fourth day, blood plasma glucose levels are determined and compared with the vehicle group. The percent change in plasma glucose levels are determined at each dose to statistical significance of $p < 0.05$.

The results of these tests are as follows:

TABLE

| Example | Dose (mg/kg) | % Change (Glucose) |
| --- | --- | --- |
| 1 | 20 | −57 |
|   | 2 | −21 |
| 2 | 20 | −58 |
|   | 5 | −41 |
|   | 2 | −20 |
| 3 | 5 | −39 |
| 4 | 5 | −41 |
| 6 | 5 | −27 |
| 7 | 5 | −42 |
| Ciglitazone Standard | 100 | −33 |

From the experimental data obtained, it is apparent that the compounds of this invention reduce blood glucose levels, which characterizes them as antihyperglycemic agents useful in the treatment of disease states involving abnormally high blood levels of glucose, such as diabetes mellitus. As such, the compounds of this invention are to be administered to a mammal suffering from excessive blood levels of glucose in an amount from about 2 mg to about 100 mg per kilogram body weight, or more, per day, in single or multiple doses. An optimum dosing regimen to achieve the desired therapeutic response must be individualized for the patient by following the post-administration glucose blood levels. The dosage will vary with the compound administered and with the patient's age, weight, severity of disease state, response, etc., as is common in all therapeutic methods for control of glucose levels.

The compounds of this invention are orally active and may be made up in conventional unit dosage forms for administration. Compositions with inert diluents or edible carriers are compressed into tablets or filled in hard or soft gelatin capsules, with sufficient active ingredient to supply a daily dose or any fraction thereof. Slow release formulations are especially suitable for control of glucose with the compounds of this invention. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aids binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurized compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions from parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active, it can be administered orally either in liquid or solid composition form.

Preferably the pharmaceutical composition is in unit dosage form, e.g. as tablets or capsules. In such form the composition is sub-divided in unit dose containing appropriate quantities of the active ingredient; the unit dosage forms can be packaged compositions, for example packeted powders, vials, ampoules, prefilled syringes or sachets containing liquids. The unit form can be, for example, a capsule or tablet itself, or it can be the appropriate number dosage of any such compositions in package form. The quantity of the active ingredient in unit dose of composition may be varied or adjusted from about 2 mg or less to 100 mg or more, according to the particular need and the activity of the active ingredient. The invention also includes the compounds in the absence of the carrier where the compounds are in unit dosage form.

What is claimed is:

1. A compound of the formulae:

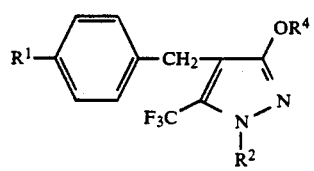 (I)

and

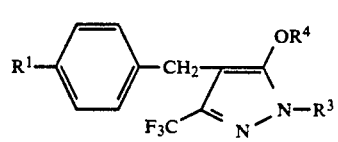 (II)

in which $R^1$ is alkyl of 1 to 6 carbon atoms, perfluoroalkyl of 1 to 6 carbon atoms, alkoxy of 1 to 6 carbon atoms, perfluoroalkoxy of 1 to 6 carbon alkylthio of 1 to 6 carbon atoms, perfluoroalkylthio of 1 to 6 carbon atoms, alkylsulfinyl of 1 to 6 carbon atoms, alkylamino of 1 to 6 carbon atoms, halo, alkanoyl of 2 to 6 carbon atoms, 1-hydroxyalkyl of 1 to 6 carbon atoms or 1-(hydroxyimino) alkyl of 1 to 6 carbon atoms;

$R^2$ is hydrogen or alkyl of 1 to 3 carbon atoms;

$R^3$ is alkyl of 1 to 3 carbon atoms;

$R^4$ is alkyl of 1 to 6 carbon atoms;

or a pharmaceutically acceptable salt thereof.

2. A compound of claim 1 of the formula:

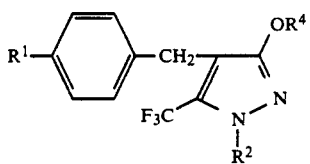

in which $R^1$ is alkyl or alkylthio of 1 to 3 carbon atoms;

$R^2$ is alkyl of 1 to 3 carbon atoms; and $R^4$ is alkyl of 1 to 6 carbon atoms;

or a pharmaceutically acceptable salt thereof.

3. A compound of claim 1 of the formula:

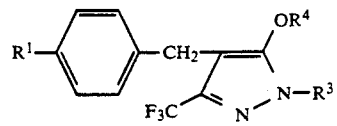

in which $R^1$ is alkyl or alkylthio of 1 to 3 carbon atoms;

$R^3$ is alkyl of 1 to 3 carbon atoms; and $R^4$ is alkyl of 1 to 6 carbon atoms;

or a pharmaceutically acceptable salt thereof.

4. The compound of claim 1 which is 3-methoxy-4-[4-(methylthiophenyl)methyl]-5-(trifluoromethyl)-1H-pyrazole, or a pharmaceutically acceptable salt thereof.

5. The compound of claim 1 which is 3-methoxy-1-methyl-4-[4-(methylthiophenyl)methyl]-5-(trifluoromethyl)pyrazole, or a pharmaceutically acceptable salt thereof.

6. The compound of claim 1 which is 4-[4-(ethylphenyl)methyl]-3-(methoxy)-5-(trifluoromethyl)-1H-pyrazole, or a pharmaceutically acceptable salt thereof.

7. The compound of claim 1 which is 4-[4-(ethylphenyl)methyl]-3-(methoxy)-1-(methyl)-5-(trifluoromethyl)pyrazole, or a pharmaceutically acceptable salt thereof.

8. The compound of claim 1 which is 3-ethoxy-1-(ethyl)-4-[4-(methylthiophenyl)methyl]-5-(trifluoromethyl)pyrazole, or a pharmaceutically acceptable salt thereof.

9. The compound of claim 1 which is 5-ethoxy-1-(ethyl)-4-[4-(methylthiophenyl)methyl]-3-(trifluoromethyl)pyrazole, or a pharmaceutically acceptable salt thereof.

10. The compound of claim 1 which is 5-methoxy-1-(methyl)-4-[(4-methylthiophenyl)methyl]-3-(trifluoromethyl)pyrazole, or a pharmaceutically acceptable salt thereof.

* * * * *